United States Patent
Schneider et al.

(12)

(10) Patent No.: US 6,391,568 B1
(45) Date of Patent: May 21, 2002

(54) METHOD FOR DETERMINING PLATELET REACTIVITY IN A WHOLE BLOOD SAMPLE

(75) Inventors: David J. Schneider, Shelburne; Burton E. Sobel, Colchester; Paula B. Tracy, Essex Jet; Paul G. Held; Paul D. Hale, both of Burlington; Norman R. Alpert, Shelburne, all of VT (US)

(73) Assignee: Lionheart Technologies, Inc., Winooski, VT (US)

( * ) Notice: Subject to any disclaimer, the term of this patent is extended or adjusted under 35 U.S.C. 154(b) by 0 days.

(21) Appl. No.: 09/115,992

(22) Filed: Jul. 15, 1998

(51) Int. Cl.[7] .................... G01N 33/533; G01N 33/536; G01N 33/577

(52) U.S. Cl. .................... 435/7.21; 435/2; 435/7.94; 435/326; 435/337; 435/288.4; 435/971; 436/536; 436/538; 436/540; 436/548; 436/63; 436/172; 436/69; 530/388.1; 530/388.2

(58) Field of Search .................... 435/2, 28, 7.1, 435/7.21, 7.94, 326, 337, 286.7, 287.1, 287.2, 288.4, 960, 971; 436/503, 522, 538, 524, 540, 536, 800, 47, 868, 63, 548, 172, 69, 164, 169; 427/2.12, 2.25; 514/9, 15; 530/388.1, 388.22

(56) References Cited

U.S. PATENT DOCUMENTS

| | | | |
|---|---|---|---|
| 5,529,902 A | | 6/1996 | Kottke et al. ............... 435/7.21 |
| 5,738,902 A | * | 4/1998 | Forrestal et al. ............ 427/2.12 |
| 5,753,617 A | * | 5/1998 | Heavner et al. ............... 514/9 |

FOREIGN PATENT DOCUMENTS

| | | |
|---|---|---|
| EP | 0273671 A | 7/1988 |
| WO | WO9106859 A | 5/1991 |
| WO | WO9413307 A | 6/1994 |
| WO | WO 95/12125 | 5/1995 |

OTHER PUBLICATIONS

D. Wen et al., "A fluorescence–conjugated immunobinding assay for the detection of P–selectin on platelets", The Journal of Laboratory and Clinical Medicine, vol. 124, No. 3, Sep. 1994, pp. 447–454.

H. Bessos et al., "A whole blood assay for platelet HPA1 (PLA1) phenotyping applicable to large–scale screening", British Journal of Haematology, vol. 92, No. 1, Jan. 1996, pp. 221–225, Abstract only.

PCT written opinion dated Jun. 21, 2000 in PCT/US99/14126.

Allman–Farinelli et al., A Simple, Whole Blood Method for Assessment of Platelet Function : Application of Dietary Intervention, Thrombosis Research, 90 (4): 163–169 (1997), Oct. 7, 1997.*

* cited by examiner

Primary Examiner—Long V. Le
Assistant Examiner—Gailene R. Gabel
(74) Attorney, Agent, or Firm—Sughrue, Mion, Zinn, Macpeak & Seas, PLLC

(57) ABSTRACT

The present invention provides a method for the quantification and assessment of platelet activation in whole blood samples and monitoring of antiplatelet pharmacologic agents. The method for quantifying platelet activation includes exposing platelets to a physiological concentration of an agonist that activates some of the platelets, resulting in the formation of at least one binding site on the surface of the activated platelets, and measuring the activated platelets. The present invention provides a method of assessing specific components of platelet activation.

56 Claims, 5 Drawing Sheets

FIG. 4

METHOD FOR DETERMINING PLATELET REACTIVITY IN A WHOLE BLOOD SAMPLE

BACKGROUND OF THE INVENTION

1. Field of the Invention

The present invention relates to a method for quantifying and assessing platelet activation in whole blood samples and monitoring the dosage of antiplatelet pharmacologic agents. The method comprises exposing platelets to a physiological concentration of an agonist that activates some of the platelets, resulting in the formation of at least one binding site on the surface of the activated platelets, and measuring the activated platelets. The present invention permits the assessment of specific components Qf platelet activation.

2. Description of the Related Art

Platelet activation is a critical component of hemostasis, the process which prevents bleeding following vascular injury. During hemostasis, platelets adhere to the site of the vascular injury. The platelets undergo activation, which leads to a change in their shape, facilitating the formation of a hemostatic plug. Platelet activation also involves a process known as degranulation, which provides the following components: proteins (e.g., Factor V and fibrinogen) and calcium necessary for the coagulation cascade; agonists (e.g., serotonin, thromboxane, and ADP) which activate and recruit additional platelets; and a negatively charged phospholipid surface on the platelet which promotes assembly and the activation of coagulation factors. An accurate assessment of platelet activation would allow clinicians to determine the risk of bleeding after invasive procedures in patients having impaired platelet function, both congenital and acquired (e.g., in association with renal failure or after ingestion of medications which alter platelet function).

Platelet activation is also critical in thrombosis, a pathologic process in which the activation of platelets and of the coagulation cascade leads to an occlusion of the blood vessel in response to atherosclerotic plaque rupture. Thrombosis complicating plaque rupture is responsible for the majority of myocardial infarctions (heart attacks) and cerebrovascular accidents (strokes). Therapy with antiplatelet agents such as aspirin, ticlopidine, and ReoPro has been shown to reduce the incidence of myocardial infarctions and cardiac death in patients having a known cardiac disease. Therapy with aspirin and ticlopidine has also been shown to reduce the incidence of stroke in patients having a cerebrovascular disease.

The major complication of antiplatelet therapy is bleeding. An accurate assessment of platelet activation would facilitate determining an optimal therapy for each patient and help reduce the incidence of thrombosis, while maintaining the hemostatic response necessary to prevent bleeding.

Conventional assays of platelet function are performed in platelet-rich plasma rather than in whole blood. Preparation of platelets for such purposes can alter their functional properties and cause assay results to be spurious. For example, platelet aggregometry assesses the aggregation of platelets and reflects the activation of the surface glycoprotein IIb-IIIa and the degranulation of platelets. This method is based on an in vitro phenomenon which has little to do with platelet function in vivo.

U.S. Pat. No. 5,529,902 discloses a fluorescence immunoassay for platelet function based on the determination of P-selectin expression. This assay suffers from the following drawbacks: (1) as in the conventional assays of platelet function, the method is performed using a platelet-rich plasma, and cannot be performed directly on whole blood samples; (2) the method is complicated by the fact that the number of platelets in each sample must be quantitated independently prior to performing the assay; (3) the assay requires that each sample be split into two portions, one of which serves as a control; and (4) the assay permits the determination of only one marker of platelet activation.

Flow cytometry has been used in conjunction with platelet surface glycoprotein-specific antibodies to determine the extent of platelet activation [see, e.g., R. E. Scharf et al., *Arteriosclerosis and Thrombosis*, 12, 1475 (1992)]. Although whole blood samples can be tested using flow cytometry-based assays, the procedures are time consuming and require expensive instrumentation, and therefore are not practical for rapidly and economically testing large numbers of samples.

Another commonly used assay of overall platelet function is the measurement of bleeding time. This procedure assesses hemostasis and only indirectly reflects the contribution of platelets and the coagulation cascade. It is notoriously insensitive regarding actual platelet function.

In summary, the critical role of platelets in hemostasis and thrombosis and the development of new, more effective antiplatelet regimens, as well as the inadequacies associated with conventional assessments of platelet function, have defined the need for an accurate assay of platelet activation. This assay would allow health care providers to define platelet reactivity and thus the risk associated with increased reactivity (thrombotic occlusion of vessels) and decreased reactivity (excess bleeding). Because each individual has a unique response to antiplatelet therapy, this assay would allow therapy to be tailored to the needs of that individual and facilitate needed adjustment of dosage over time.

SUMMARY OF THE INVENTION

To solve the above problems, it is an object of the present invention to provide an improved method for the assessment of platelet activation in whole blood samples. Unlike conventional assays of platelet function, such as platelet aggregometry and bleeding times, the present invention permits the assessment of specific components of platelet activation. Thus, this assay facilitates a determination of increased platelet reactivity and thus the risk associated with increased reactivity (thrombotic occlusion of vessels) and decreased reactivity (excess bleeding) This assay also facilitates a determination of the adequacy of inhibition of reactivity secondary to treatment with antiplatelet regimens with regard to specific components of platelet activation. Accordingly, because each individual subject has a unique response to antiplatelet therapy, this assay allows therapy to be tailored to the needs of each individual patient and facilitate appropriate dosage adjustment over time in each.

The specific components of platelet activation include the following: activation of the surface glycoprotein IIb-IIIa which reveals a binding site for fibrinogen and thus allows for the crosslinking of platelets by fibrinogen [see, e.g., S. J. Shattil et al., Blood, 70,307(1987), and C. S. Abrams et al., Blood, 75, 128 (1990)]; the release of the contents of the alpha granules, in which degranulation leads to the release of stored proteins and to the expression of the integrin P-selectin on the surface of the platelet [see, e.g., J. N. George et al., J. Clin. Invest., 78, 340 (1986)]; the release of the contents of the dense granules, in which degranulation leads to the release of nucleotides and calcium; the release of the contents of lysosomes, in which degranulation leads to the release of stored proteins; the procoagulant effect whereby platelets facilitate assembly and activity of coagulation factors; and shape change whereby platelets increase surface area thereby facilitating formation of a hemostatic plug.

In order to accurately reflect the reactivity of platelets, the present invention provides a method of determining the extent of platelet activation in response to physiologic concentrations of an agonist. After exposure to such an agonist, the platelets are exposed to solutions containing the following: fluorochrome-labeled ligands which bind to all platelets, both activated and quiescent; fluorochrome-labeled ligands which bind only to activated platelets; and biotin conjugated ligands which facilitate the binding of platelets to a solid phase. After exposing the platelets to a fixative (e.g., formaldehyde), the platelets are bound to a solid phase by exposure to a streptavidin or avidin coated surface.

The interaction of platelets with the coated surface is preferably facilitated by centrifugation. Unbound fluorochrome-labeled ligands are preferably removed by washing.

The specific components of platelet activation are preferably determined by measuring the fluorescent signal intensities emitted by each of the bound activation-dependent fluorochrome-labeled ligands, and emitted by the fluorochrome-labeled marker of all platelets.

BRIEF DESCRIPTION OF THE DRAWINGS

The present invention will be understood and appreciated more fully from the following detailed description taken in conjunction with the drawings in which.

DETAILED DESCRIPTION OF THE INVENTION

The present invention provides a method for the assessment of specific components of platelet activation in blood samples. In the preferred embodiment of this invention, whole blood samples are used because platelet reactivity may be altered by the methods used to obtain purified platelet preparations or by the removal of selected blood components.

In the preferred embodiment of the invention, the artificial activation of coagulation which occurs after blood is exposed to foreign surfaces must be prevented because this artificial activation alters platelet reactivity. Exposure of blood to a foreign surface activates a protein, Factor XII, which in turn initiates the coagulation cascade leading to the generation of thrombin; thrombin activates platelets and forms fibrin. On the other hand, the initiation of the coagulation cascade in vivo after vascular injury does not involve the activation of Factor XII. Vascular injury causes blood to be exposed to tissue factor, which complexes with Factor VIIa and initiates the coagulation cascade. Accordingly, in the preferred embodiment of the invention, artificial activation of the coagulation cascade is prevented by inhibiting Factor XIIa, while the remainder of the coagulation cascade is left intact due to its interplay with the activation of platelets.

Thus, in the preferred embodiment of the invention, the assessment of platelet activation is carried out using whole blood samples preferably treated only with corn trypsin inhibitor, a specific inhibitor of Factor XIIa with no effect on other coagulation factors. Other anticoagulants, such as chelate calcium, would be avoided as they have been shown to cause artificial enhancement of ADP-induced platelet activation.

In the preferred embodiment of the invention, the extent of platelet activation is determined in response to physiologic concentrations of an agonist, such as, but not limited to, ADP (adenosine 5'-diphosphate) or TRAP (thrombin receptor agonist peptide). After exposure to such an agonist, the platelets are exposed to the following solutions (A-D), either simultaneously or sequentially:

(A) A solution containing fluorochrome-labeled ligands which bind to all platelets, both activated and quiescent; examples of such fluorochrome-labeled ligands include, but are not limited to, fluorochrome-labeled antibodies which bind to all platelets.

(B) A solution containing fluorochrome-labeled ligands which bind only to activated platelets; examples of such fluorochrome-labeled ligands include, but are not limited to, fluorochrome-labeled antibodies which bind to P-selectin on the surface of activated platelets, or fluorochrome-labeled fibrinogen which binds to sites on the surface of activated platelets.

(C) A solution containing ligands which facilitate the binding of all platelets to a solid phase; examples of such ligands include, but are not limited to, biotin-labeled antibodies which bind to all platelets.

(D) A solution containing a fixative, which prevents further platelet activation; examples of such a fixative include, but are not limited to, 1.5% formaldehyde.

Interaction between platelets and the solid phase may be enhanced by centrifuging the samples after adding the samples to a vessel such as microtitration plates.

After binding the platelets to a solid phase including, but not limited to, at least one well of a microtitration plate, unbound fluorochrome-labeled ligands are removed by washing, and the specific components of platelet activation are determined by measuring the fluorescent signal intensities emitted by each of the bound activation-dependent fluorochrome-labeled ligands, and emitted by the fluorochrome-labeled marker of all platelets.

The manner in which the assessment of specific components of platelet activation is performed can be understood more fully by reference to the following illustrative examples, which are not intended to limit the scope of the invention in any way.

EXAMPLE 1

Figure 1:
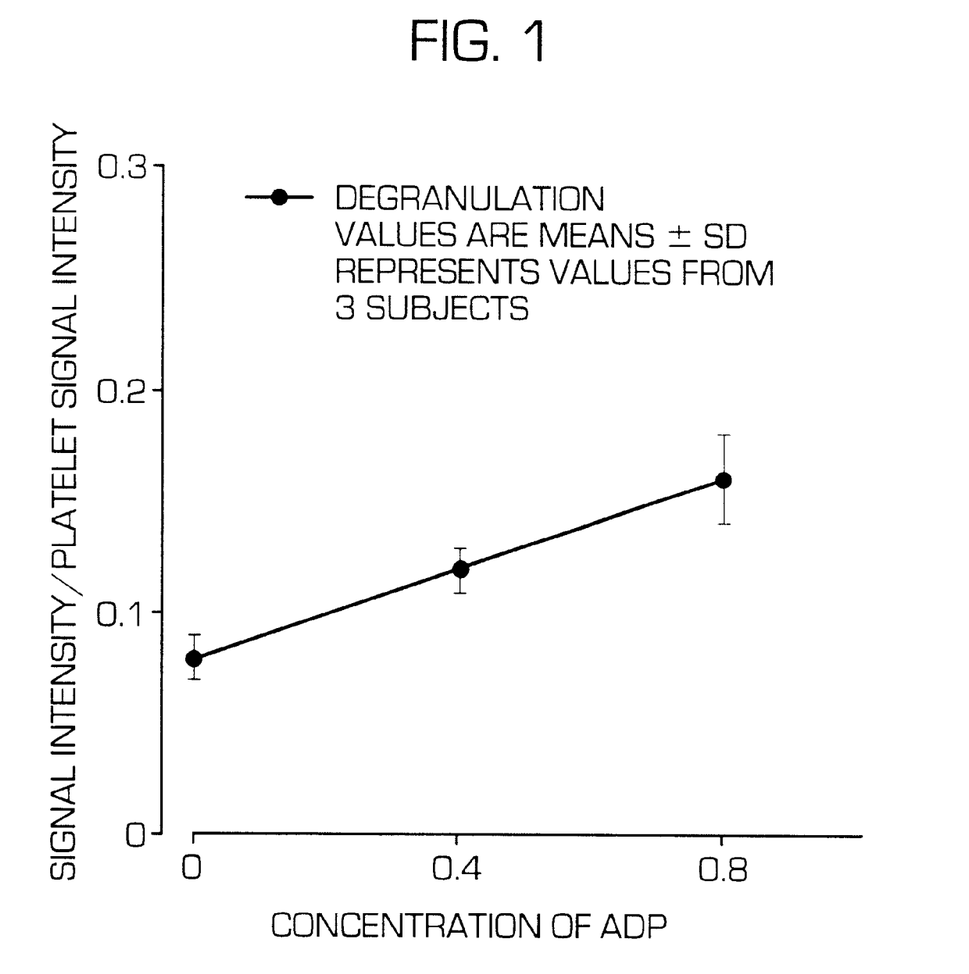
FIG. 1 is a graphic illustration of the extent of platelet activation caused by exposure of a whole blood sample to selected concentrations of the agonist ADP (adenosine 5'-diphosphate), in which platelet activation is defined as the ratio between the fluorescent signal produced by fluorochrome-labeled antibodies bound to a protein, P-selectin, on the surface of activated platelets and the fluorescent signal produced by fluorochrome-labeled antibodies bound to all platelets in the reaction vessel.

Capture of Platelets in Microtitration Wells and Determination of Platelet Activation by Measurement of the Extent of P-selectin Expression on the Platelet Surface P-selectin is an integral membrane protein in the alpha granules of platelets. During platelet activation, alpha granule exocytosis results in fusion of the granule membrane with the platelet membrane, bringing P-selectin to the platelet membrane surface. The expression of P-selectin can be measured by capturing platelets with an immobilized antibody in a microtitration well, and then using two fluorescent markers: CD42*PerCP (an IgG antibody to glycoprotein IX, with PerCP as the fluorescent label) which marks all platelets, and CD62*PE (an IgG antibody to P-selectin, with phycoerythrin as the fluorescent label) which marks platelets expressing P-selectin and thus marks those platelets which are activated. Two concentrations of ADP, a weak agonist, are used to activate the platelets, and the dose response of platelets to ADP is characterized in whole blood. By using fixed doses of ADP, it is possible to determine the extent of platelet activation in each sample, and the efficacy of antiplatelet therapy can be determined by analyzing the slope of individual response curves or by the activation in response to a selected concentration of the agonist, as shown in FIG. 1.

Similar results were obtained with parallel experiments in which the association of labeled ligands with platelets was determined by using flow cytometry. When a flow cytometry determination of the association of ligands with platelets is made, in the absence of added agonists, minimal platelet activation is observed (i.e., less than 1 percent of platelets are activated in the absence of agonists when P-selectin is used as the marker for activation).

EXAMPLE 1 PROCEDURE

Phlebotomy was performed by using a two syringe technique whereby the first 3 ml of blood were discarded. Activation of platelets was delineated in blood drawn directly into a syringe containing 32 µg/ml of corn trypsin inhibitor (CTI, 9:1 v/v), an agent which inhibits Factor XIIa without affecting other coagulation factors. The CTI was used as an anticoagulant to prevent activation of the contact factor pathway and permit analysis of activation of platelets dependent on addition of exogenous activators. Unlike CTI, other anticoagulants, particularly chelators of calcium such as citrate, alter the activation of platelets. 5 µl of blood were added to microcentrifuge tubes containing Hepes Tyrodes buffer (5 mM HEPES, 137 mM NaCl, 2.7 mM NaHCO$_3$, 0.36 mM NaH$_2$PO$_4$, 2 mM CaCl$_2$, 4 mM MgCl$_2$, and 5 mM dextrose, pH 7.4), a PerCP conjugated IgG directed against glycoprotein IX (CD 42a), a phycoerythrin (PE) conjugated IgG directed against P-selectin (CD 62), a biotin conjugated antibody directed against glycoprotein IIb (CD 41), and selected concentrations of ADP (0, 0.4, 0.8 µM). CD 42a binds to an activation independent epitope on glycoprotein IX and thus was used to tag and hence identify all platelets. The biotin conjugated CD 41 binds to an activation independent epitope on glycoprotein IIb and thus serves as the ligand to capture platelets. P-selectin is expressed on the surface of only activated platelets and thus serves to mark platelets which have degranulated. After adding blood, the reaction solution was mixed gently and incubated at room temperature for 15 minutes. The platelets were fixed, and the red blood cells were lysed by adding optilyses-C (1.5% formaldehyde) after a 15 minute incubation. The reaction mixture was then added to a streptavidin-coated well in a microtitration plate. The plate was centrifuged (1000×g for 15 minutes) to optimize the interaction between the platelets and the solid phase. The wells were then washed three times with Hepes Tyrodes buffer. The intensity of fluorescence for each ligand was determined with a microplate fluorescent plate reader.

EXAMPLE 2

Figure 2:
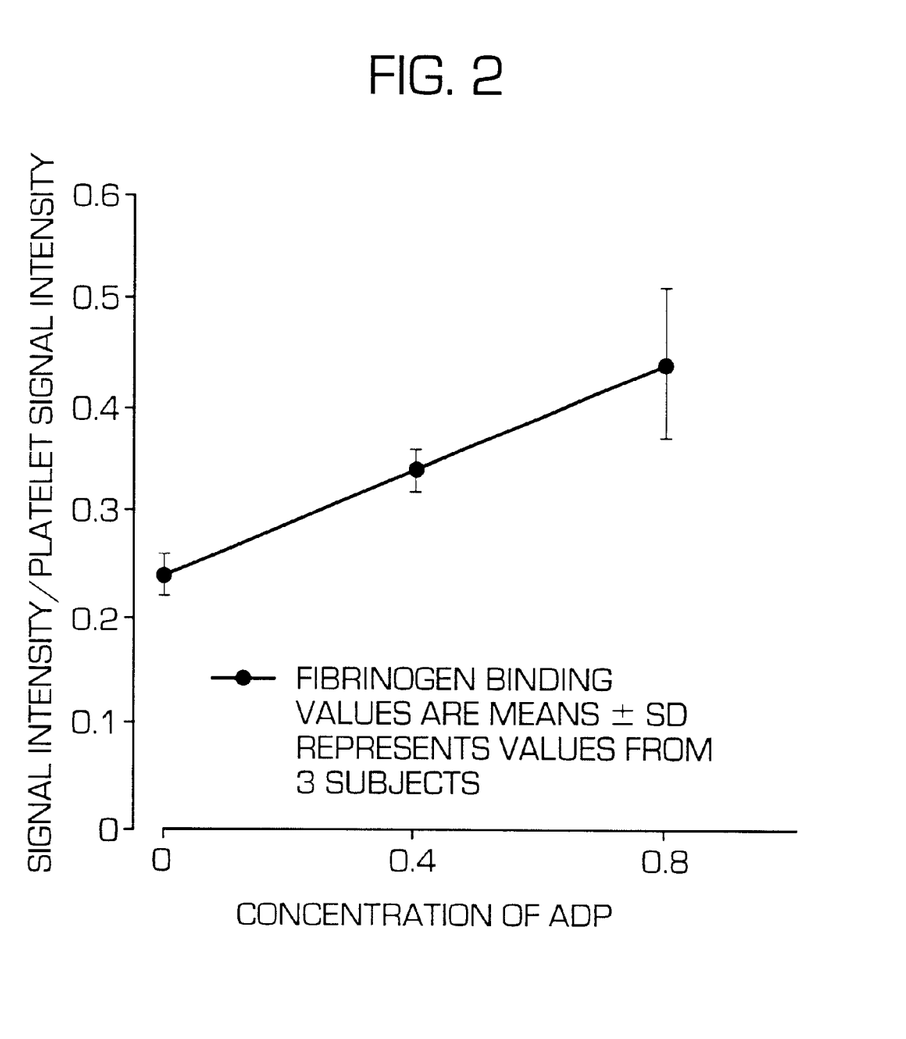
FIG. 2 is a graphic illustration of the extent of platelet activation caused by exposure of a whole blood sample to selected concentrations of the agonist ADP, in which platelet activation is defined as the ratio between the fluorescent signal produced by fluorochrome-labeled fibrinogen bound to the surface of activated platelets and the fluorescent signal produced by fluorochrome-labeled antibodies bound to all platelets in the reaction vessel.

Capture of Platelets in Microtitration Wells and Determination of Platelet Activation by Measurement of the Extent of Fibrinogen Binding on the Platelet Surface Platelet activation is also reflected in the activation of the surface glycoprotein IIb-IIIa which reveals a binding site for fibrinogen. The extent of fibrinogen binding can be measured by capturing platelets with an immobilized antibody in a microtitration well, and then using two fluorescent markers: CD42*PerCP (an IgG antibody to glycoprotein IX, with PerCP as the fluorescent label) which marks all platelets; and fibrinogen*FITC (fibrinogen conjugated with fluorescein isothiocyanate as the fluorescent label) which marks platelets in which activation of surface glycoprotein IIb-IIIa has occurred. Two concentrations of ADP are used to activate the platelets, and the dose response of platelets to ADP is characterized in whole blood. By using fixed doses of ADP, it is possible to determine the extent of platelet activation in each sample. The efficacy of antiplatelet therapy can be determined by analyzing the slope of individual response curves or by the activation in response to a selected concentration of the agonist, as shown in FIG. 2.

EXAMPLE 2 PROCEDURE

Phlebotomy was performed by using a two syringe technique whereby the first 3 ml of blood were discarded. Activation of platelets was delineated in blood drawn directly into a syringe containing 32 µg/ml of corn trypsin inhibitor (CTI, 9:1 v/v), an agent which inhibits Factor XIIa without affecting other coagulation factors. The CTI was used as an anticoagulant to prevent the activation of the contact factor pathway and permit an analysis of platelet activation dependent on the addition of exogenous activators. CTI was used rather than other anticoagulants because unlike CTI, other anticoagulants, particularly chelators of calcium such as citrate, alter the activation of platelets. 5 µl of blood were added to microcentrifuge tubes containing Hepes Tyrodes buffer (5 mM HEPES, 137 mM NaCl, 2.7 mM NaHCO$_3$, 0.36 mM NaH$_2$PO$_4$, 2 mM CaCl$_2$, 4 mM MgCl$_2$, and 5 mM dextrose, pH 7.4), a PerCP conjugated IgG directed against glycoprotein IX (CD 42a), fibrinogen conjugated to fluorescein isothiocyanate (FITC), a biotin conjugated antibody directed against glycoprotein IIb (CD 41), and selected concentrations of ADP (0, 0.4, 0.8 µM). CD 42a binds to an activation independent epitope on glycoprotein IX and thus was used to tag and hence identify all platelets. The biotin conjugated CD 41 binds to an activation independent epitope on glycoprotein IIb and thus serves as the ligand to capture platelets. Fibrinogen binds to the surface of platelets only when the surface glycoprotein IIb-IIIa is activated and thus serves to identify activated platelets. After adding blood, the reaction solution was mixed gently and incubated at room temperature for 15 minutes. The platelets were fixed, and the red blood cells were lysed by adding Optilyse-C (1.5% formaldehyde) after the 15 minute incubation. The reaction mixture was then added to a streptavidin-coated well in a microtitration plate. The plate was centrifuged (1000×g for 15 minutes) to optimize the interaction between the platelets and the solid phase. The wells were then washed three times with Hepes Tyrodes buffer. The intensity of fluorescence for each ligand was determined with a microplate fluorescent plate reader.

EXAMPLE 3

Figure 3:
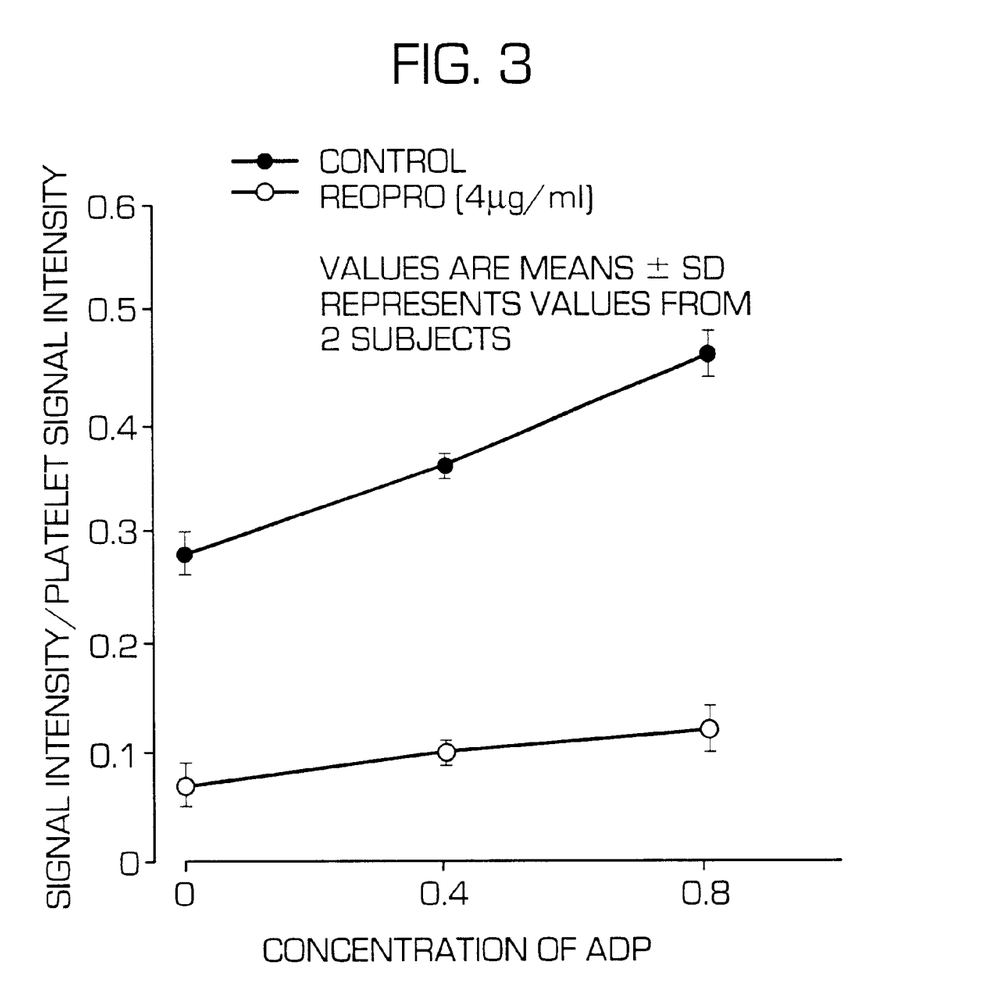
FIG. 3 is a graphic illustration of the decrease in platelet activation caused by the antiplatelet drug ReoPro, where the extent of platelet activation, caused by exposure of a whole blood sample to selected concentrations of the agonist ADP, is defined as the ratio between the fluorescent signal produced by fluorochrome-labeled fibrinogen bound to the surface of activated platelets and the fluorescent signal produced by fluorochrome-labeled antibodies bound to all platelets in the reaction vessel.

Capture of Platelets in Microtitration Wells and Determination of Inhibition of Fibrinogen Binding to Platelets by ReoPro Platelet activation is inhibited by the drug ReoPro, and is reflected by the inhibition of binding of fibrinogen to the activated conformer of the surface glycoprotein IIb-IIIa. The extent of fibrinogen binding can be measured by capturing platelets with an immobilized antibody in a microtitration well, and then using two fluorescent markers: CD42*PerCP (an IgG antibody to glycoprotein IX, with PerCP as the fluorescent label) which marks all platelets; and fibrinogen*FITC (fibrinogen conjugated with fluorescein isothiocyanate as the fluorescent label) which marks platelets in which an activation of surface glycoprotein IIb-IIIa has occurred. Two concentrations of ADP are used to activate the platelets, and the dose response of platelets to ADP is characterized in whole blood and in whole blood spiked with ReoPro. The concentration of ReoPro used is that known to inhibit the aggregation of platelets as determined with the use of aggregometry. As shown in FIG. 3, pretreatment of blood with ReoPro inhibits binding of fibrinogen*FITC to platelets.

EXAMPLE 3 PROCEDURE

Phlebotomy was performed by using a two syringe technique whereby the first 3 ml of blood were discarded. Activation of platelets was delineated in blood drawn directly into a syringe containing 32 µg/ml of corn trypsin inhibitor (CTI, 9:1 v/v) and into a syringe containing CTI (32 µg/ml) plus ReoPro (3 µg/ml). 5 µl of blood were added to microcentrifuge tubes containing Hepes Tyrodes buffer (5 mM HEPES, 137 mM NaCl, 2.7 mM NaHCO$_3$, 0.36 mM NaH$_2$PO$_4$, 2 mM CaCl$_2$, 4 mM MgCl$_2$, and 5 mM dextrose, pH 7.4), a PerCP conjugated IgG directed against glycoprotein IX (CD 42a), fibrinogen conjugated to fluorescein isothiocyanate (FITC), a biotin conjugated antibody directed against glycoprotein IIb (CD 41), and selected concentrations of ADP (0, 0.4, 0.8 µM). CD 42a binds to an activation independent epitope on glycoprotein IX and thus was used to tag and hence identify all platelets. The biotin conjugated CD 41 binds to an activation independent epitope on glycoprotein IIb and thus serves as the ligand to capture platelets. Fibrinogen binds to the surface of platelets only when the surface glycoprotein IIb-IIIa is activated and thus serves to identify activated platelets. After adding blood, the reaction solution was mixed gently and incubated at room temperature for 15 minutes. The platelets were fixed, and the red blood cells were lysed by adding Optilyse-C (1.5% formaldehyde) after the 15 minute incubation. The reaction mixture was then added to a streptavidin-coated well in a microtitration plate. The plate was centrifuged (1000×g for 15 minutes) to optimize the interaction between the platelets and the solid phase. The wells were then washed three times with Hepes Tyrodes buffer. The intensity of fluorescence for each ligand was determined with a microplate fluorescent plate reader.

EXAMPLE 4

Figure 4:
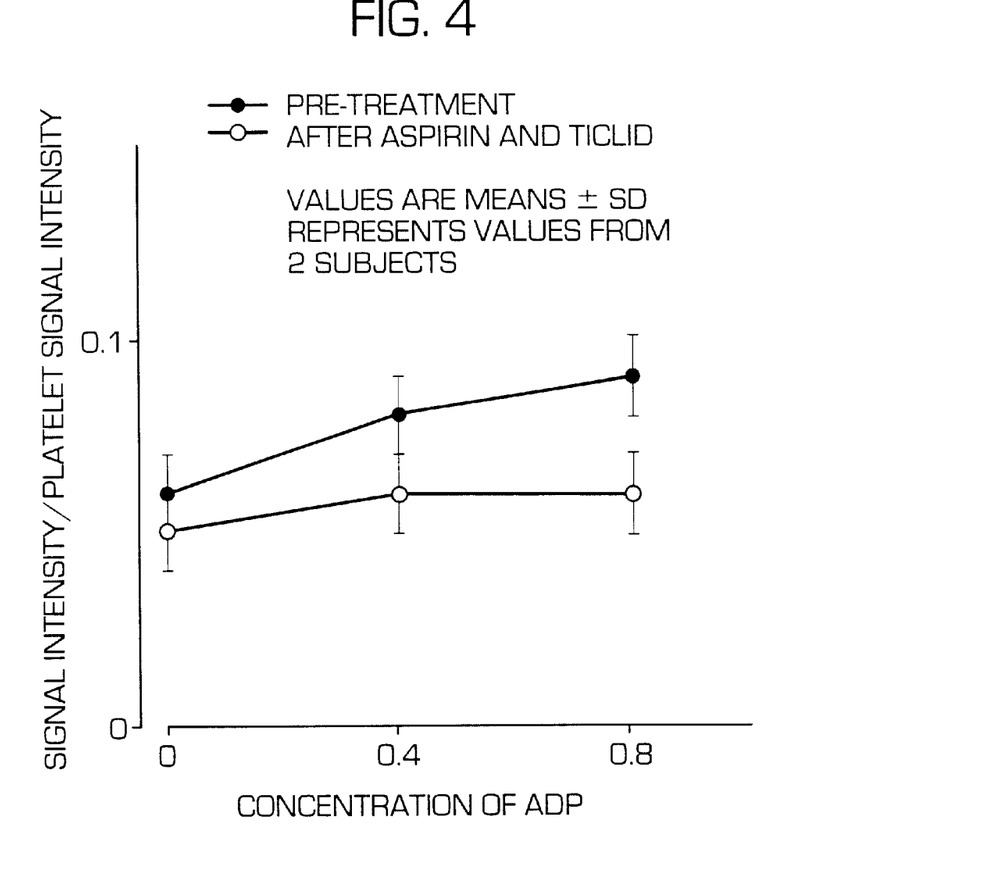
FIG. 4 is a graphic illustration of the decrease in platelet activation caused by the antiplatelet drugs aspirin and Ticlid, where the extent of platelet activation, caused by exposure of a whole blood sample to selected concentrations of the agonist ADP, is defined as the ratio between the fluorescent signal produced by fluorochrome-labeled antibodies bound to P-selectin on the surface of activated platelets and the fluorescent signal produced by fluorochrome-labeled antibodies bound to all platelets in the reaction vessel.

Capture of Platelets in Microtitration Wells and Determination of Inhibition of Degranulation after Ingestion of Aspirin and Ticlid Platelet activation is inhibited after ingestion of two antiplatelet agents, aspirin and Ticlid. Degranulation in response to ADP was determined before and after ingestion of aspirin and Ticlid by capturing platelets with an immobilized antibody in a microtitration well, and then using two fluorescent markers: CD42*PerCP (an IgG antibody to glycoprotein IX, with PerCP as the fluorescent label) which marks all platelets; and CD62*PE (a phycoerythrin [PE] conjugated IgG directed against P-selectin). P-selectin is expressed on the surface of only activated platelets and thus serves to mark platelets which have degranulated. Two concentrations of ADP are used to activate the platelets, and the dose response of platelets to ADP is characterized in whole blood obtained from subjects before and after 4 days of ingestion of aspirin (325 mg/day) and Ticlid (250 mg BID). As shown in FIG. 4, ingestion of aspirin and Ticlid inhibits ADP-induced degranulation of platelets.

EXAMPLE 4 PROCEDURE

Phlebotomy was performed by using a two syringe technique whereby the first 3 ml of blood were discarded. Activation of platelets was delineated in blood drawn directly into a syringe containing 32 µg/ml of corn trypsin inhibitor (CTI, 9:1 v/v). 5 µl of blood were added to microcentrifuge tubes containing Hepes Tyrodes buffer (5 mM HEPES, 137 mM NaCl, 2.7 mM NaHCO$_3$, 0.36 mM NaH$_2$PO$_4$, 2 mM CaCl$_2$, 4 mM MgCl$_2$, and 5 mM dextrose, pH 7.4), a PerCP conjugated IgG directed against glycoprotein IX (CD 42a), CD 42 conjugated to phycoerythrin (PE), a biotin conjugated antibody directed against glycoprotein IIb (CD 41), and selected concentrations of ADP (0, 0.4, 0.8 µM). CD 42a binds to an activation independent epitope on glycoprotein IX and thus was used to tag and hence identify all platelets. The biotin conjugated CD 41 binds to an activation independent epitope on glycoprotein IIb and thus serves as the ligand to capture platelets. CD 42 binds to the surface of platelets only when degranulation has occurred and P-selectin is expressed on the surface of the platelet. After adding blood, the reaction solution was mixed gently and incubated at room temperature for 15 minutes. The platelets were fixed, and the red blood cells were lysed by adding Optilyse-C (1.5% formaldehyde) after the 15 minute incubation. The reaction mixture was then added to a streptavidin-coated well in a microtitration plate. The plate was, centrifuged (1000×g for 15 minutes) to optimize the interaction between the platelets and the solid phase. The wells were then washed three times with Hepes Tyrodes buffer. The intensity of fluorescence for each ligand was determined with a microplate fluorescent plate reader.

EXAMPLE 5

Figure 5:
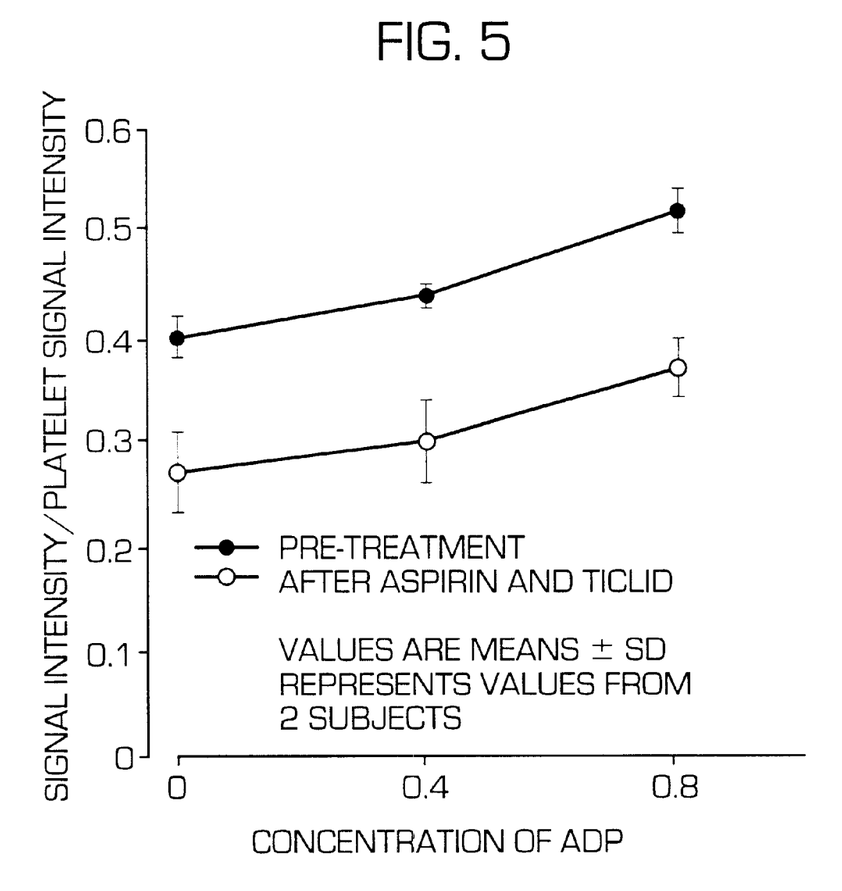
FIG. 5 is a graphic illustration of the decrease in platelet activation caused by the antiplatelet drugs aspirin and Ticlid, where the extent of platelet activation, caused by exposure of a whole blood sample to selected concentrations of the agonist ADP, is defined as the ratio between the fluorescent signal produced by fluorochrome-labeled fibrinogen bound to the surface of activated platelets and the fluorescent signal produced by fluorochrome-labeled antibodies bound to all platelets in the reaction vessel.

Capture of Platelets in Microtitration Wells and Determination of Inhibition of Fibrinogen Binding after Ingestion of Aspirin and Ticlid Platelet activation is inhibited after ingestion of two antiplatelet agents, aspirin and Ticlid. Activation of glycoprotein IIb-IIIa in response to ADP was determined before and after ingestion of aspirin and Ticlid by capturing platelets with an immobilized antibody in a microtitration well, and then using two fluorescent markers: CD42*PerCP (an IgG antibody to glycoprotein IX, with PerCP as the fluorescent label) which marks all platelets; and fibrinogen*FITC (fibrinogen conjugated to fluorescein isothiocyanate [FITC]). Fibrinogen binds to the activated conformer of the surface glycoprotein IIb-IIIa. Two concentrations of ADP are used to activate the platelets, and the dose response of platelets to ADP is characterized in whole blood obtained from subjects before and after 4 days of ingestion of aspirin (325 mg/day) and Ticlid (250 mg BID). As shown in FIG. 5, the ingestion of aspirin and ticlid inhibits ADP-induced binding of fibrinogen to platelets.

EXAMPLE 5 PROCEDURE

Phlebotomy was performed by using a two syringe technique whereby the first 3 ml of blood were discarded. Activation of platelets was delineated in blood drawn directly into a syringe containing 32 $\mu$g/ml of corn trypsin inhibitor (CTI, 9:1 v/v). 5 $\mu$l of blood were added to microcentrifuge tubes containing Hepes Tyrodes buffer (5 mM HEPES, 137 mM NaCl, 2.7 mM NaHCO$_3$, 0.36 mM NaH$_2$PO$_4$, 2 mM CaCl$_2$, 4 mM MgCl$_2$, and 5 mM dextrose, pH 7.4), a PerCP conjugated IgG directed against glycoprotein IX (CD 42a), fibrinogen conjugated to fluorescein isothiocyanate (FITC), a biotin conjugated antibody directed against glycoprotein IIb (CD 41), and selected concentrations of ADP (0, 0.4,0.8 $\mu$M). CD 42a binds to an activation independent epitope on glycoprotein IX and thus was used to tag and hence identify all platelets. The biotin conjugated CD 41 binds to an activation independent epitope on glycoprotein IIb and thus serves as the ligand to capture platelets. Fibrinogen binds to the surface of platelets when the surface glycoprotein IIb-IIIa is activated. After adding blood, the reaction solution was mixed gently and incubated at room temperature for 15 minutes. The platelets were fixed, and the red blood cells were lysed by adding Optilyse-C (1.5% formaldehyde) after the 15 minute incubation. The reaction mixture was then added to a streptavidin-coated well in a microtitration plate. The plate was centrifuged (1000×g for 15 minutes) to optimize the interaction between the platelets and the solid phase. The wells were then washed three times with Hepes Tyrodes buffer. The intensity of fluorescence for each ligand was determined with a microplate fluorescent plate reader.

While particular embodiments of the invention have been described, it will be understood, of course, that the invention is not limited thereto, and that many modifications and variations can be made by those skilled in the art, and that such modifications and variations are intended to fall within the scope of the appended claims.

What is claimed is:

1. A method for measuring platelet reactivity in a whole blood sample without preparing a platelet-rich preparation, consisting essentially of:
    (A) activating a portion of the platelets in the whole blood sample by adding to the sample an amount of a platelet agonist, thereby providing the whole blood sample containing activated platelets and unactivated platelets;
    (B) exposing the whole blood sample from (A) to the following agents:
        an activation-dependent fluorochrome-labeled ligand comprising a ligand that binds one form more activated platelets;
        an activation-independent fluorochrome-labeled ligand comprising a ligand that binds both said activated platelets and said unactivated platelets;
        a binding ligand which binds all platelets to a solid surface;
        a fixative which prevents further platelet activation;
    (C) exposing the whole blood sample from (B) to a solid surface having a moiety that binds said binding ligand which binds all platelets to a solid surface, to allow binding of all platelets to the solid surface;
    (D) measuring fluoroscence of the activation-dependent fluorochrome-labeled ligand and the activation-independent fluorochrome-labeled ligand; and
    (E) determining a ratio of fluorescence of the activation-dependent fluorochrome-labeled ligand to the activation-independent fluorochrome-labeled ligand, thereby measuring platelet reactivity.

2. The method of claim 1, wherein the platelet agonist is adenosine 5'-diphosphate (ADP).

3. The method of claim 2, wherein the concentration of ADP is 0.4 $\mu$M.

4. The method of claim 2, wherein the concentration of ADP is 0.8 $\mu$M.

5. The method of claim 1, wherein the platelet agonist is thrombin receptor agonist peptide (TRAP).

6. The method of claim 1, wherein the activation-dependent fluorochrome-labeled ligand binds to a protein expressed by the activated platelets as a result of activation.

7. The method of claim 6, wherein the protein expressed by the activated platelets as a result of activation is P-selectin.

8. The method of claim 1, wherein the activation-dependent fluorochrome-labeled ligand is a fluorochrome-labeled anti-P-selectin antibody.

9. The method of claim 1, wherein the activation-dependent fluorochrome-labeled ligand is a fluorochrome-labeled fibrinogen.

10. The method of claim 1, wherein the activation-independent fluorochrome-labeled ligand is a fluorochrome-labeled antibody.

11. The method of claim 10, wherein the fluorochrome-labeled antibody is a fluorochrome-labeled anti-glycoprotein IX antibody.

12. The method of claim 1, wherein the binding ligand which binds all platelets to a solid surface is a biotin-conjugated antibody.

13. The method of claim 12, wherein the biotin-conjugated antibody conjugated anti-glycoprotein IIb antibody.

14. The method of claim 1, wherein the fixative is formaldehyde.

15. The method of claim 1, wherein said moiety that binds said binding ligand is streptavidin or avidin.

16. The method of claim 1 or 15, wherein the solid surface is at least one well of a microtitration plate.

17. The method of claim 16, further comprising centrifuging the microtitration plate to increase binding of all platelets to the solid surface during the exposing step (C).

18. The method of claim 17, further comprising post-centrifugation washing of the at least one well of the microtitration plate prior to measuring fluorescence.

19. The method of claim 1, further comprising using a microplate fluorescence reader to measure fluorescence.

20. The method of claim 1, wherein the agonist in step (A) and the agents set forth in step (B) are added to the whole blood sample simultaneously.

21. The method of claim 1, wherein the agonist in step (A) and the agents set forth in step (B) are added to the whole blood sample sequentially.

22. A method for measuring platelet reactivity in a whole blood sample without preparing a platelet-rich preparation, consisting essentially of:
(A) activating a portion of the platelets in the whole blood sample by adding to the sample an amount of a platelet agonist that also induces expression of at least one binding site for fibrinogen on the surface of each activated platelet, thereby providing the whole blood sample containing activated platelets and unactivated platelets;
(B) exposing the whole blood sample from (A) to the following agents:
fluorochrome-labeled fibrinogen;
an activation-dependent fluorochrome-labeled ligand comprising a ligand that binds both said activated platelets and unactivated platelets;
a binding ligand which binds all platelets to a solid surface;
a fixative which prevents further platelet activation;
(C) exposing the whole blood sample from (B) to a solid surface having a moiety that binds said binding ligand which binds all platelets to a solid surface, to allow binding of all platelets to the solid surface;
(D) measuring fluorescence of the fluorochrome-labeled fibrinogen and the activation-independent fluorochrome-labeled ligand; and
(E) determining a ratio of fluorescence of the fluorochrome-labeled fibrinogen to the activation-independent fluorochrome-labeled ligand, thereby determining platelet reactivity.

23. The method of claim 22, wherein the platelet agonist is ADP.

24. The method of claim 23, wherein the concentration of ADP is 0.4 $\mu$M.

25. The method of claim 23, wherein the concentration of ADP is 0.8 $\mu$M.

26. The method of claim 22, wherein the platelet agonist is TRAP.

27. The method of claim 22, wherein the activation-independent fluorochrome-labeled ligand is a fluorochrome-labeled antibody.

28. The method of claim 27, wherein the fluorochrome-labeled antibody is a fluorochrome-labeled anti-glycoprotein IX antibody.

29. The method of claim 22, wherein the binding ligand which binds all platelets to a solid surface is a biotin-conjugated antibody.

30. The method of claim 29, wherein the biotin-conjugated is biotin anti-glycoprotein IIb antibody.

31. The method of claim 22, wherein the fixative is formaldehyde.

32. The method of claim 22, wherein said moiety that binds said binding ligand is streptavidin or avidin.

33. The method of claim 22 or 32, wherein the solid surface is at least one well of a microtitration plate.

34. The method of claim 33, further comprising centrifuging the microtitration plate to increase binding of all platelets to the solid surface during the exposing step (C).

35. The method of claim 34, further comprising post-centrifugation washing of the at least one well of the microtitration plate prior to measuring fluorescence.

36. The method of claim 22, further comprising using a microplate fluorescence reader to measure fluorescence.

37. The method of claim 22, wherein the agonist in step (A) and the agents set forth in step (B) are added to the whole blood sample simultaneously.

38. The method of claim 22, wherein the agonist in step (A) and the agents set forth in step (B) are added to the whole blood sample sequentially.

39. A method for measuring platelet reactivity in a whole blood sample without preparing a platelet-rich preparation, consisting essentially of:
(A) activating a portion of the platelets in the whole blood sample by adding to the sample an amount of a platelet agonist that also induces expression of P-selectin of the surface of each activated platelet, thereby providing the whole blood sample containing activated platelets and unactivated platelets;
(B) exposing the whole blood sample from (A) to the following agents:
fluorochrome-labeled ligand that binds P-selectin;
an activation-independent fluorochrome-labeled ligand comprising a ligand that binds both said activated platelets and unactivated platelets;
a binding ligand which binds all platelets to a solid surface;
a fixative which prevents further platelet activation;
(C) exposing the whole blood sample from (B) to a solid surface having a moiety that binds said binding ligand which binds all platelets to a solid surface, to allow binding of all platelets to the solid surface;
(D) measuring fluoroscence of the fluorochrome-labeled ligand that binds P-selectin and the activation-independent fluorochrome-labeled ligand; and
(E) determining a ratio of fluorescence of the fluorochrome-labeled ligand that binds P-selectin to the activation-independent fluorochrome-labeled ligand, thereby determining platelet reactivity.

40. The method of claim 39, wherein the platelet agonist is ADP.

41. The method of claim 40, wherein the concentration of ADP is 0.4 $\mu$M.

42. The method of claim 40, wherein the concentration of ADP is 0.8 $\mu$M.

43. The method of claim 39, wherein the platelet agonist is TRAP.

44. The method of claim 39, wherein the fluorochrome-labeled ligand that binds P-selectin is a fluorochrome-labeled anti-P-selectin antibody.

45. The method of claim 39, wherein the activation-independent fluorochrome-labeled ligand is a fluorochrome-labeled antibody.

46. The method of claim 45, wherein the fluorochrome-labeled antibody is a fluorochrome-labeled anti-glycoprotein IX antibody.

47. The method of claim 1, wherein the binding ligand which binds all platelets to a solid surface is a biotin-conjugated antibody.

48. The method of claim 47, wherein the biotin-conjugated antibody is biotin conjugated anti-glycoprotein IIb antibody.

49. The method of claim 39, wherein the fixative is formaldehyde.

50. Missing.

51. The method of claim 39 or 50, wherein the solid surface is at least one well of a microtitration plate.

52. The method of claim 51, further comprising centrifuging the microtitration plate to increase binding of all platelets to the solid surface during the exposing step (C).

53. The method of claim 52, further comprising post-centrifugation washing of the at least one well of the microtitration plate prior to measuring fluorescence.

54. The method of claim 39, further comprising using a microplate fluorescence reader to measure fluorescence.

55. The method of claim 39, wherein the agonist in step (A) and the agents set forth in step (B) are added to the whole blood sample simultaneously.

56. The method of claim 39, wherein the agonist in step (A) and the agents set forth in step (B) are added to the whole blood sample sequentially.

* * * * *

UNITED STATES PATENT AND TRADEMARK OFFICE
CERTIFICATE OF CORRECTION

PATENT NO. : 6,391,568 B1
DATED : May 21, 2002
INVENTOR(S) : David J. Schneider et al.

It is certified that error appears in the above-identified patent and that said Letters Patent is hereby corrected as shown below:

Column 1,
Line 16, change "Qf" to -- of --.

Column 10,
Line 15, change "form" to -- or --.
Line 64, after "antibody", insert -- is biotin --.

Column 11,
Line 32, change "activation-dependent" to -- activation-independent --.
Line 34, after "and", insert -- said --.
Line 66, after "method", insert -- conjugated --.
Line 67, after "conjugated", insert -- antibody --.

Column 12,
Line 26, change "of" (second occurrence) to -- on --.
Line 35, after "and", insert -- said --.

Column 13,
Line 1, change "claim 1" to -- claim 39 --.
Line 9, change "missing" to -- The method of claim 39, wherein said moiety that binds said binding ligand is streptavidin or avidin --.

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,391,568 B1
DATED         : May 21, 2001
INVENTOR(S)   : Schneider, David J. et al.

It is certified that error appears in the above-identified patent and that said Letters Patent is hereby corrected as shown below:

Column 1,
Line 5, after the title, please add the following:
-- STATEMENT REGARDING GOVERNMENT SPONSORED RESEARCH OR DEVELOPMENT:
This invention was made with Government support under Grant No. EPS-9703938 awarded by the National Science Foundation. The Government may have certain rights in this invention. --.

Signed and Sealed this

Second Day of August, 2005

JON W. DUDAS
*Director of the United States Patent and Trademark Office*